(12) United States Patent
Mueller

(10) Patent No.: US 7,407,926 B2
(45) Date of Patent: Aug. 5, 2008

(54) OIL-CONTAINING SURFACTANT GELS COMPRISING A MIXTURE OF ETHOXYLATED CITRIC ACID ESTERS

(75) Inventor: Michael Mueller, Monhelm (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 11/263,009

(22) Filed: Oct. 31, 2005

(65) Prior Publication Data

US 2006/0105929 A1 May 18, 2006

(30) Foreign Application Priority Data

Nov. 12, 2004 (DE) .................... 10 2004 054 842

(51) Int. Cl.
*C11D 1/24* (2006.01)
*C11D 7/18* (2006.01)

(52) U.S. Cl. .................. 510/479; 510/130; 510/158; 510/208; 510/251; 510/372; 510/375; 510/403; 510/421; 510/434; 510/367; 510/370; 510/318; 510/361

(58) Field of Classification Search ............... 510/119, 510/123, 124, 125, 127, 130, 158, 208, 251, 510/367, 372, 403, 318, 361, 370, 375, 421, 510/434, 479
See application file for complete search history.

(56) References Cited

U.S. PATENT DOCUMENTS

| 4,070,309 | A | * | 1/1978 | Jacobsen ................. 510/236 |
| 5,302,377 | A | * | 4/1994 | Pereira et al. ............. 424/59 |
| 5,456,745 | A | * | 10/1995 | Roreger et al. ......... 106/140.1 |
| 5,523,025 | A | * | 6/1996 | Erilli ..................... 510/417 |
| 6,235,914 | B1 | * | 5/2001 | Steiger et al. ............ 554/114 |
| 6,376,455 | B1 | * | 4/2002 | Friedli et al. ............. 510/515 |
| 6,413,527 | B1 | * | 7/2002 | Simonnet et al. ......... 424/401 |
| 6,998,426 | B2 | * | 2/2006 | L'Alloret et al. .......... 523/102 |
| 2006/0105929 | A1 | * | 5/2006 | Mueller .................. 510/130 |
| 2006/0110415 | A1 | * | 5/2006 | Gupta .................... 424/401 |

* cited by examiner

*Primary Examiner*—Charles I Boyer
(74) *Attorney, Agent, or Firm*—John F. Daniels

(57) ABSTRACT

The invention relates to gel-form cosmetic preparations containing
(a) 5 to 50% by weight of surfactants;
(b) 5 to 50% by weight of oils and/or waxes;
(c) 0 to 15% by weight of water-soluble polyols; and
component (a) contains at least 10% by weight, based on component (a) as a whole, of a mixture of citric acid esters of alkoxylated alcohols and the sum of components (a) and (b) in the preparation as a whole being from 10 to 70% by weight.

19 Claims, No Drawings

OIL-CONTAINING SURFACTANT GELS COMPRISING A MIXTURE OF ETHOXYLATED CITRIC ACID ESTERS

CROSS-REFERENCE TO RELATED APPLICATIONS

This application claims priority from German application number DE 102004054842.0 filed Nov. 12, 2004, the entire contents of which are incorporated herein by reference.

FIELD OF THE INVENTION

This invention relates generally to surfactant-containing gels used as cosmetic preparations.

BACKGROUND OF THE INVENTION

Water-based surfactant formulations normally have a very limited uptake capacity for care components, such as oils and waxes. If the transparency and the thermodynamic stability of the surfactant formulation are to be maintained, only small quantities of oils or waxes can be incorporated, based on the weight of the surfactant. An exception are microemulsions of which some allow the incorporation of more than 100% by weight of oils, based on surfactant. However, microemulsions are low in viscosity while their stability is highly temperature-dependent according to the type of surfactant used. The low viscosity of microemulsions seriously restricts their scope of application in cosmetic products, because a high viscosity is required for feel and for application of the cosmetic product to the body.

The use of the usual thickeners also involves disadvantages because they can be deposited on the skin and hair and the thickened preparations often do not have the required stability.

Accordingly, the problem addressed by the present invention was to provide cosmetic surfactant-containing gel formulations which would contain oil and/or waxes and which would be stable without the use of thickeners. The gels would have high dimensional stability and would be transparent or slightly opaque in appearance. In addition, they would have a very good feeling on the skin.

BRIEF DESCRIPTION OF THE INVENTION

The present invention relates to gel-form cosmetic preparations containing:
(a) 5 to 50% by weight of surfactants;
(b) 5 to 50% by weight of oils and/or waxes;
(c) 0 to 15% by weight of water-soluble polyols;

component (a) containing at least 10% by weight, based on component (a) as a whole, of a mixture of citric acid esters of alkoxylated alcohols and the sum of components (a) and (b) in the preparation as a whole being from 10 to 70% by weight.

It has surprisingly been found that, by using citric acid esters of alkoxylated alcohols as the basic surfactant, it is possible to obtain surfactant formulations of high to very high viscosity which can accommodate up to 300% by weight of oils or waxes, based on surfactant. The extremely high-viscosity formulations are gels which show pronounced dimensional stability and are transparent or slightly opaque in appearance. The gel-form preparations according to the invention are free from polymeric thickeners.

DETAILED DESCRIPTION OF THE INVENTION

Component (a)

The gel-form preparations according to the invention may contain other surfactants besides the citric acid esters of alkoxylated alcohols. In one particular embodiment, the preparations according to the invention contain co-surfactants selected from the group consisting of anionic, cationic, nonionic, amphoteric and/or zwitterionic surfactants besides citric acid esters of alkoxylated alcohols as component (a).

Anionic Surfactants

Typical examples of anionic surfactants are soaps, alkyl benzene-sulfonates, alkane sulfonates, olefin sulfonates, α-methyl ester sulfonates, sulfofatty acids, alkyl sulfates, alkyl ether sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acyl amino acids such as, for example, acyl lactylates, acyl tartrates, acyl glutamates and acyl aspartates, alkyl oligoglucoside sulfates and protein fatty acid condensates (especially wheat-based vegetable products).

Cationic Surfactants

Typical example of cationic surfactants are quaternary ammonium compounds and esterquats, more particularly quaternized fatty acid trialkanolamine ester salts.

Nonionic Surfactants

Typical examples of nonionic surfactants are alk(en)yl oligoglycosides, fatty acid-N-alkyl glucamides, polyol fatty acid esters, sugar esters, sorbitan esters, polysorbates, alcohol ethoxylates and amine oxides. Preferred nonionic surfactants are alkyl and/or alkenyl oligoglucosides which correspond in particular to formula (II):

$$R^2O\text{-}[G]_p \qquad (II)$$

where $R^2$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (II) indicates the degree of oligomerization (DP), i.e. the distribution of mono- and oligoglycosides, and is a number of 1 to 10. Whereas p in a given compound must always be an integer and, preferably has a value of 1 to 6, the value p for a certain alkyl oligoglycoside is an analytically determined calculated quantity which is generally a broken number. Alkyl and/or alkenyl oligo-glycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational perspective.

The alkyl or alkenyl group $R^2$ may be derived from primary alcohols containing 4 to 22 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligo-glucosides based on technical $C_{9/11}$ oxoalcohols (DP=1 to 3) are preferred. In addition, the alkyl or alkenyl group $R^2$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Alcohol ethoxylates are known from their production as fatty alcohol or oxoalcohol ethoxylates and preferably correspond to formula (III):

(III)

in which $R^1$ is a linear or branched alkyl and/or alkenyl group containing 6 to 22 carbon atoms and n is a number of 1 to 50. Typical examples are adducts of on average 1 to 50, preferably 5 to 40 and more particularly 10 to 25 mol ethylene oxide with caproic alcohol, caprylic alcohol, 2-ethylhexyl alcohol, capric alcohol, lauryl alcohol, isotridecyl alcohol, myristyl alcohol, cetyl alcohol, palmitolelyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Adducts of 10 to 40 mol ethylene oxide with technical $C_{12-18}$ fatty alcohols, such as for example coconut oil, palm oil, palm kernel oil or tallow fatty alcohol, are preferred.

Zwitterionic and Amphoteric Surfactants

Examples of suitable amphoteric or zwitterionic surfactants are alkyl betaines, alkyl amidobetaines, aminopropionates, aminoglycinates, imidazolinium betaines and sulfobetaines. Examples of suitable alkyl betaines are the carboxyalkylation products of secondary and, in particular, tertiary amines corresponding to formula (IV):

in which $R^3$ represents alkyl and/or alkenyl groups containing 6 to 22 carbon atoms, $R^4$ represents hydrogen or alkyl groups containing 1 to 4 carbon atoms, $R^5$ represents alkyl groups containing 1 to 4 carbon atoms, q1 is a number of 1 to 6 and Z is an alkali metal and/or alkaline earth metal or ammonium. Typical examples are the carboxymethylation products of hexylmethyl amine, hexyldimethyl amine, octyldimethyl amine, decyldimethyl amine, dodecylmethyl amine, dodecyldimethyl amine, dodecylethylmethyl amine, $C_{12/14}$ cocoalkyldimethyl amine, myristyldimethyl amine, cetyldimethyl amine, stearyldimethyl amine, stearylethylmethyl amine, oleyldimethyl amine, $C_{16/18}$ tallow alkyldimethyl amine and technical mixtures thereof.

Also suitable are carboxyalkylation products of amidoamines corresponding to formula (V):

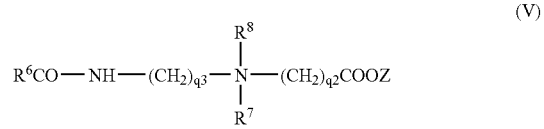

in which $R^6CO$ is an aliphatic acyl group containing 6 to 22 carbon atoms and 0 or 1 to 3 double bonds, $R^7$ is hydrogen or represents alkyl groups containing 1 to 4 carbon atoms, $R^8$ represents alkyl groups containing 1 to 4 carbon atoms, q2 is a number of 1 to 6, q3 is a number of 1 to 3 and Z is again an alkali metal and/or alkaline earth metal or ammonium. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethyl amine, N,N-dimethylaminopropyl amine, N,N-diethylaminoethyl amine and N,N-diethylaminopropyl amine which are condensed with sodium chloroacetate. A condensation product of $C_{8/18}$-cocofatty acid-N,N-dimethylaminopropyl amide with sodium chloroacetate is preferably used.

Imidazolinium betaines may also be used. These compounds are also known compounds which may be obtained, for example, by cyclizing condensation of 1 or 2 moles of fatty acid with polyfunctional amines such as, for example, aminoethyl ethanolamine, (AEEA) or diethylenetriamine. The corresponding carboxyalkylation products are mixtures of different open-chain betaines. Typical examples are condensation products of the fatty acids mentioned above with AEEA, preferably imidazolines based on lauric acid or—again—$C_{12/14}$ cocofatty acid which are subsequently betainized with sodium chloroacetate.

Particularly preferred preparations in the context of the present invention are those where component (a), in addition to citric acid esters of alkoxylated alcohols, contains co-surfactants selected from the group consisting of betaines, acylated amino acids, alkylether sulfates, alkyl sulfates and alkyl oligoglycosides.

Citric Acid Ester Mixtures of Alkoxylated Alcohols

Citric acid ester mixtures of alkoxylated alcohols are used as the basic surfactant of component (a). The preferred basic surfactant of component (a) are mixtures of citric acid esters of mixtures of ethoxylated alcohols corresponding to general formula (I):

$$R^1O(CH_2CH_2O)_nH \quad (I)$$

in which $R^1$ is a linear alkyl group containing 4 to 24 carbon atoms and n is a number of 5 to 9, with the proviso that the ratio by weight of monoester to diester in the citric acid ester mixtures is in the range from 3:1 to 10:1.

The citric acid ester mixtures of component (a) are anionic surfactants, i.e. mainly compounds which still contain at least one free carboxyl group. Accordingly, they may be acidic esters or neutralization products thereof. The partial esters are preferably present in the form of the alkali metal, alkaline earth metal, ammonium, alkylammonium, alkanolammonium and/or glucammonium salts.

The citric acid ester mixtures are derived from alkoxylated alcohols, preferably from alkoxylated aliphatic alcohols containing 4 to 24 carbon atoms. The citric acid ester mixtures are preferably derived from ethoxylated alcohols containing 4 to 24 carbon atoms and more particularly from those corresponding to general formula (II):

$$R^2O(CH_2CH_2O)_nH \quad (II)$$

in which $R^2$ is a linear or branched alkyl and/or alkenyl group containing 4 to 24 carbon atoms and n is a number of 1 to 50. Compounds of formula (II) with a degree of ethoxylation n of 1 to 20 are preferred. Typical examples are adducts of on average 1 to 20, preferably 1 to 10 and more particularly 1 to 8 mol ethylene oxide with caproic alcohol, caprylic alcohol, 2-ethylhexyl alcohol, capric alcohol, lauryl alcohol, isotridecyl alcohol, myristyl alcohol, cetyl alcohol, palmitolelyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Adducts of 1 to 10 mol ethylene oxide with technical $C_{12-18}$ fatty alcohols, such as for example coconut oil, palm oil, palm kernel oil or tallow fatty alcohol, are preferred. A particularly suitable fatty alcohol mixture contains 65 to 75% by weight $C_{12}$, 20 to 30% by weight $C_{14}$, 0 to 5% by weight $C_{16}$ and 0 to 5% by weight $C_{18}$ alcohols. This alcohol mixture is commercially available, for example, as Dehydol LS™ from Cognis Deutschland GmbH & Co. KG. Another particularly suitable fatty alcohol mixture contains 45 to 60% by weight $C_{12}$, 15 to 30% by weight $C_{14}$, 5 to 15% by weight $C_{16}$ and 8 to 20% by weight $C_{18}$ alcohols. This alcohol mixture is also commercially available, for example, as Dehydol LT™ from Cognis Deutschland GmbH & Co. KG.

Component (b)

The formulations according to the invention contain as component (b) oils and/or waxes which have skin- and hair-care properties.

Both non-polar and polar oils or mixtures thereof may be used as component (b). Such oils include, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as for example Dicaprylyl Carbonate (Cetiol® CC), Guerbet carbonates based on $C_{8-16}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as for example Dicaprylyl Ether (Cetiol® OE), ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes or silicone oils or, in a particularly preferred embodiment, Hydrogenated Polydecene.

However, solid fats and/or waxes may also be used as component (b). They may be present in admixture with the oils mentioned in the previous paragraph. Typical examples of fats are glycerides, i.e. solid or liquid, vegetable or animal products which consist essentially of mixed glycerol esters of higher fatty acids. Solid mono- and diglycerides, such as glycerol monooleate or glycerol monostearate for example, are particularly mentioned in this regard. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides fats, fat-like substances, such as lecithins and phospholipids, are suitable additives. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable as component (b), as are tocopherols and essential oils.

Component (c)

The gel-form preparations according to the invention may optionally contain mono- or polyhydric alcohols containing 1 to 4 carbon atoms in a quantity of 0 to 15% by weight, based on the formulation as a whole. In a preferred embodiment, the preparations according to the invention contain glycerol, ethylene glycol and/or propylene glycol as component (c). The addition of these alcohols increases the uptake capacity of the preparations for oils. In addition, the refractive index of the water phase can be adapted to that of the dispersed oil phase so that possible clouding is reduced. In addition, the storage stability of the gels at low temperatures, for example at $-5°$ C., is increased.

Hydrogen Peroxide

In another preferred embodiment, the preparations according to the invention contain hydrogen peroxide. The dimensionally stable gels according to the invention are easy to apply to the hair and, after application, remain in close contact with the hair, i.e. do not drip off like a liquid, by virtue of their high dimensional stability.

The preparations according to the invention are produced by stirring with a simple stirrer at temperatures of ca. 70° C. Very high stirring speeds are not necessary. If wax components are to be incorporated, they must be heated before stirring to temperatures beyond their melting point.

EXAMPLES

The Examples in the following Tables show the ingredients in % by weight active substance. The Tables show not only the INCI name of the active substance, but also the trade name of a corresponding commercial product.

TABLE 1

| INCI Trade name | Oil gels Concentration [% by wt. active substance] | | | | | | |
|---|---|---|---|---|---|---|---|
| Glyceryl Oleate Monomuls ® 90-018 | 8.00 | 6.88 | 8.00 | 8.00 | 8.00 | 8.00 | 8.00 |
| Dicaprylyl Ether Cetiol ® OE | 30.00 | 25.80 | 30.00 | 30.00 | — | — | — |
| Paraffin oil | — | — | — | — | 30.00 | 30.00 | 30.00 |
| Laureth-7 Citrate Plantapon ® LC7 | 15.00 | 12.90 | 15.00 | 15.00 | 15.00 | 15.00 | 11.50 |
| Lauryl Glucoside Plantacare ® 1200 UP | 8.40 | 7.23 | 7.06 | 5.04 | 5.04 | 7.56 | 8.57 |
| 1,2-Propylene glycol | 3.00 | — | — | — | — | — | — |
| NaCl | — | 1.08 | — | — | — | 1.00 | — |
| Deionized water | 35.60 | 46.11 | 39.94 | 41.96 | 41.96 | 38.44 | 41.93 |
| Appearance | Slightly cloudy Gel | Slightly opaque gel-like formulation | Relatively clear gel | Clear gel | Clear gel | Clear gel | Clear gel |
| pH (with 15% NaOH) | 4.40 | 4.34 | 3.75 | 3.73 | 5.22 | 3.70 | 4.68 |

TABLE 2

Oil gels

| INCI Trade name | Concentration [% by wt. active substance] | | | |
|---|---|---|---|---|
| Glyceryl Oleate Monomuls ® 90-018 | 8.00 | 6.88 | 8.00 | 8.00 |
| Dicaprylyl Ether Cetiol ® OE | 30.00 | 25.80 | 30.00 | 30.00 |
| Laureth-7 Citrate Plantapon ® LC7 | 15.00 | 12.90 | 15.00 | 15.00 |
| Sodium Lauryl Glucose Carboxylate (and) Lauryl Glucoside Plantapon ® LGC SORB | 4.21 | — | — | — |
| Disodium Cocoamphodiacetate Dehyton ® DC | — | 7.17 | 7.00 | 5.00 |
| 1,2-Propylene glycol | 3.00 | — | — | — |
| NaCl | — | 1.08 | — | — |
| Deionized water | 39.79 | 46.17 | 40.00 | 42.00 |
| Appearance | Clear, gel-like | Opaque, gel-like | Relatively clear, gel-like | Slightly opaque, gel-like |
| pH (with 15% NaOH) | 4.05 | 4.06 | 4.16 | 3.88 |

TABLE 3

Oil gels

| INCI Trade name | Concentration [% by wt. active substance] | | | | | |
|---|---|---|---|---|---|---|
| Glyceryl Oleate Monomuls ® 90-018 | 8.00 | 8.00 | 8.00 | 8.00 | 8.00 | 8.00 |
| Dicaprylyl Ether Cetiol ® OE | 30.00 | 30.00 | 30.00 | 30.00 | 30.00 | 30.00 |
| Laureth-7 Citrate Plantapon ® LC7 | 15.00 | 15.00 | 15.00 | 15.00 | 15.00 | 15.00 |
| Sodium Myreth Sulfate Texapon ® K 14 spez. 70% | 11.66 | 11.66 | 11.66 | — | — | — |
| Sodium Laureth Sulfate (and) Sodium Laureth-8 Sulfate (and) Magnesium Laureth Sulfate (and) Sodium Laureth-8 Sulfate (and) Sodium Oleth Sulfate (and) Magnesium Oleth Sulfate Texapon ® ASV 50 | — | — | — | 8.33 | — | — |
| Sodium Lauroyl Sarcosinate Plantapon ® LS 30 | — | — | — | — | 4.76 | 4.76 |
| 1.2-Propylene glycol | — | — | 3.00 | 3.00 | — | — |
| NaCl | 1.25 | — | — | — | — | 1.25 |
| Deionized water | 34.09 | 35.34 | 32.34 | 35.67 | 42.24 | 40.99 |
| Appearance | Relatively cloudy gel | Clear gel | Clear gel | Relatively cloudy gel | Relatively clear gel | Relatively cloudy gel |
| pH (with 15% NaOH) | 5.12 | 3.87 | 4.30 | 4.00 | 5.16 | 4.50 |

TABLE 4

Gel containing hydrogen peroxide

| INCI Trade name | Concentration [% by wt. active substance] |
|---|---|
| Glyceryl Oleate Monomuls ® 90-018 | 8.00 |
| Dicaprylyl Ether Cetiol ® OE | 30.00 |
| Laureth-7 Citrate Plantapon ® LC7 | 15.00 |
| Lauryl Glucoside Plantacare ® 1200 UP | 7.06 |
| Hydrogen peroxide | 3.00 |
| Deionized water | 36.94 |
| Appearance | Clear, gel-like |

The invention claimed is:

1. A gel-form cosmetic preparation comprising:
   (a) 5 to 50% by weight of surfactants;
   (b) 5 to 50% by weight of oils and/or waxes;
   (c) 0 to 15% by weight of water-soluble polyols;
   wherein, component (a) contains at least 10% by weight, based on component (a) as a whole, of a mixture of citric acid esters of alkoxylated alcohols of the formula $R^1O(CH_2CH_2O)_nH$, wherein, $R^1$ is a linear or branched alkyl or alkenyl group containing 4 to 24 carbon atoms, and n is a number of from 1 to 50 and a sum of components (a) and (b) in the preparation as a whole being from 10 to 70% by weight, and with the proviso that the ratio by weight of monoester to diester in the citric acid ester mixture is in a range of 3:1 to 10:1.

2. The preparation as claimed in claim 1, wherein, in addition to the citric acid esters of alkoxylated alcohols, component (a) contains at least one co-surfactant selected from the group consisting of anionic, cationic, non ionic, amphoteric and zwitterionic surfactants.

3. The preparation as claimed in claim 2, wherein, component (a) contains at least one co-surfactant selected from the group consisting of betaines, acylated amino acids, alkyl ether sulfates, alkyl sulfates and alkyl oligoglycosides.

4. The preparation as claimed in claim 1, wherein, component (a) comprises a mixture of esters of citric acid of ethoxylated alcohols of the formula:

$$R^1O(CH_2CH_2O)_nH \qquad (I)$$

in which $R^1$ is a linear alkyl group containing 4 to 24 carbon atoms and n is a number of 5 to 9.

5. The preparation of claim 1, wherein, component (c) comprises at least one member selected from the group consisting of glycerol, ethylene glycol and propylene glycol.

6. The preparation of claim 1, wherein, the preparation additionally contains hydrogen peroxide.

7. The preparation of claim 1, wherein, the preparation additionally contains water.

8. The preparation of claim 2, wherein, component (a) comprises a mixture of esters of citric acid of ethoxylated alcohols of the formula:

$$R^1O(CH_2CH_2O)_nH \qquad (I)$$

in which $R^1$ is a linear or branched alkyl or alkenyl group containing 4 to 24 carbon atoms and n is a number of 1 to 20.

9. The preparation of claim 8, wherein, component (c) comprises at least one member selected from the group consisting of glycerol, ethylene glycol and propylene glycol.

10. The preparation of claim 9, wherein, the preparation additionally contains hydrogen peroxide.

11. The preparation of claim 8, wherein, the preparation additionally contains water.

12. The preparation of claim 3, wherein, component (a) comprises a mixture of esters of citric acid of ethoxylated alcohols of the formula:

$$R^1O(CH_2CH_2O)_nH \qquad (I)$$

in which $R^1$ is a linear or branched alkyl or alkenyl group containing 4 to 24 carbon atoms and n is a number of 1 to 10.

13. The preparation of claim 12, wherein, component (c) comprises at least one member selected from the group consisting of glycerol, ethylene glycol and propylene glycol.

14. The preparation of claim 13, wherein, the preparation additionally contains hydrogen peroxide.

15. The preparation of claim 12, wherein, the preparation additionally contains water.

16. The preparation of claim 4, wherein, component (c) comprises at least one member selected from the group consisting of glycerol, ethylene glycol and propylene glycol.

17. The preparation of claim 4, wherein, the preparation additionally contains hydrogen peroxide.

18. The preparation of claim 4, wherein, the preparation additionally contains water.

19. The preparation of claim 5, wherein, the preparation additionally contains water.

* * * * *